United States Patent [19]

Glazener

[11] 4,261,355

[45] Apr. 14, 1981

[54] CONSTANT POSITIVE PRESSURE BREATHING APPARATUS

[76] Inventor: Edwin L. Glazener, 2109 Guy St., San Diego, Calif. 92103

[21] Appl. No.: 945,452

[22] Filed: Sep. 25, 1978

[51] Int. Cl.³ ............................................ A61M 16/00
[52] U.S. Cl. ............................................... 128/204.25
[58] Field of Search ............... 128/145.5, 145.6, 145.7, 128/145.8, 142.3, 188, 203, 202, 201, 208, 209, 210, 184, 147, 142 R, 142.2, 142.5, 142.7, 173 R, 194, 204, 205, 351, 277, 204.25, 203.12, 205.12, 205.18, 204.18, 205.23; 137/604, DIG. 9

[56] References Cited

U.S. PATENT DOCUMENTS

| | | | |
|---|---|---|---|
| 2,280,050 | 4/1942 | Alexander et al. | 128/145.5 |
| 3,128,994 | 4/1964 | Hungate | 137/604 X |
| 3,485,243 | 12/1969 | Bird et al. | 128/145.8 |
| 3,565,068 | 2/1971 | Bickford | 128/142 |
| 3,628,532 | 12/1971 | Magrath | 128/145.8 |
| 3,714,944 | 2/1973 | Price et al. | 128/209 |
| 3,842,828 | 10/1974 | Bird | 128/145.8 |
| 3,850,197 | 11/1974 | Ernst | 128/145.5 X |
| 3,881,479 | 5/1975 | Carden | 128/145.8 |
| 3,991,762 | 11/1976 | Radford | 128/351 X |
| 4,030,492 | 6/1977 | Simbruner | 128/205.24 X |

FOREIGN PATENT DOCUMENTS

| | | | |
|---|---|---|---|
| 2013463 | 4/1970 | France | 128/351 |
| 578109 | 6/1958 | Italy | 128/204.25 |
| 1462182 | 1/1977 | United Kingdom | 128/145.8 |

Primary Examiner—Henry J. Recla
Attorney, Agent, or Firm—Bruno J. Verbeck; Michael L. Slonecker

[57] ABSTRACT

An anesthetist's device for inducing constant positive pressure within the airway passages of a patient, adaptable for use with a mouthpiece, a mask, or in conjunction with an endotracheal tube. Said device comprises a hollow, cylindrical channel serving as a conduit for gases either spontaneously or mechanically aspired by a patient. Interposed into said channel is a narrow diameter nozzle venting compressed gas in the direction of inspired flow. By regulating the mass flow rate of compressed gas through said nozzle, variable levels of constant positive airway pressure can be produced.

4 Claims, 4 Drawing Figures

CONSTANT POSITIVE PRESSURE BREATHING APPARATUS

BACKGROUND OF THE INVENTION

This invention relates to a unique, hygienic, disposable and low cost device whereby constant airway-passage positive pressure in patients undergoing either spontaneous respiration or mechanical ventilation may be created and maintained.

During the past few years, studies conducted by members of the medical profession have demonstrated that continuous positive pressure breathing (CPPB) substantially aids in the prevention and treatment of the adult respiratory distress syndrome. This technique basically involves pressurization of a patient's lungs, whereby a slight pressure prevails in the lungs at the termination of the expiration cycle, thereby preventing alveolar collapse.

Apparatus hitherto employed with CPPB techniques have generally proven to be bulky, complicated, and expensive to operate. Still further, such apparatus greatly increase the risk of infectious cross-contamination when used by several different patients.

A recent advance in the art which mitigates some of the aforementioned drawbacks is disclosed in Carden, British Pat. No. 1,462,182. This CPPB device is particularly designed for use with neonates experiencing respiratory distress. However, it too possesses significant limitations making it generally unsuitable for use with adult patients. Inasmuch as expired air must pass through restricted orifices before exiting the device, dangerously high levels of back pressure can be created should a patient cough. Furthermore, the presence of these orifices precludes the use of extubation devices for fluid removal from airway passages.

Therefore, it is an object of this invention to produce a light weight, inexpensive, disposable device which is convenient to handle and which substantially reduces cross-contamination risks.

A still further object is to produce a device readily adaptable for use with endotracheal tubes, masks, and mouthpieces.

Yet another object is to provide a device which eliminates the danger of high airway passage back pressure should a patient cough while using said device.

Still another object is to provide a device which permits the concurrent use of endotracheal suction apparatus.

Yet another object is to produce a device readily compatible for use with mechanical ventilation equipment whereby both continuous positive pressure and controlled mechanical ventilation may be administered to a patient using same.

SUMMARY OF THE INVENTION

Briefly, the invention comprises a hollow, unobstructed, cylindrical channel serving as a conduit for gases spontaneously or mechanically aspired by a patient. Radially interposed into said channel is a narrow diameter nozzle possessing an exit aperture directed towards the patient. Said nozzle further projects radially outward from the outer wall of said channel, forming a nipple, thereby permitting connection of the device, via flexible tubing, to a remote gas reservoir.

In normal use, spontaneously or mechanically ventilated gas communicates to a patient through said channel. Superimposed upon the aspired gas is a constant and steady state stream of pressurized gas vented through the exit aperture of the narrow diameter nozzle, and toward the airway passages of the patient. Control of the mass flow rate of gas from the remote reservoir through said nozzle permits the maintenance of constant positive airway pressure at all times during the respiratory cycle.

DESCRIPTION OF THE PREFERRED EMBODIMENT

Figure 1:
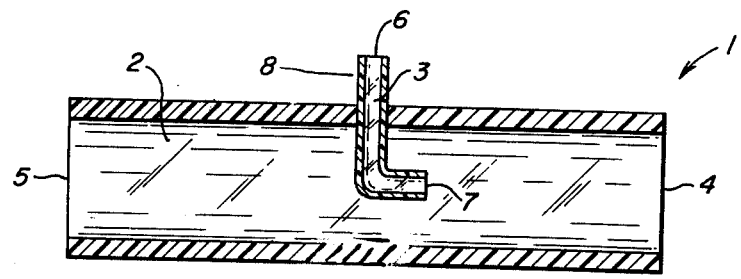
FIG. 1 is a longitudinal cross-sectional view of the preferred embodiment of my invention.

For a more complete understanding of my invention, reference may be made to FIG. 1, illustrating the preferred embodiment of my device. The device, generally referred to as 1, is exhibited as comprising two elements, a primary channel 2 and a narrow diameter nozzle 3. Though FIG. 1 shows channel 2 and nozzle 3 as separate elements, it is contemplated that normal manufacture of device 1 would be as a single integrated unit constructed of rigid plastic or metal.

More specifically, channel 2 comprises a hollow, thinwalled, cylindrical conduit possessing an inlet aperture 5 and an outlet aperture 4. Aperture 5 may either open to ambient air, as when a patient undergoes spontaneous respiration, or may be attached by friction fitting adapters to conventional flexible tubing, and thence to a mechanical ventilator providing the patient with controlled and conditioned gas. Aperture 4 is directed toward the patient and may be attached by adapters to either endotracheal tubes, mouthpieces, or masks.

As configured, channel 2 has a constant inner diameter nominally 7-10mm. This diameter is sufficiently large to ensure that no significant resistance to aspired gas flow is created. Further, the inner volume of channel 2 is sufficiently small to prevent the build up of excessive and dangerous levels of expired carbon dioxide gas.

Nozzle 3 is a constant diameter cylindrical conduit radially interposed through the outer wall of channel 2, bending to a right angle along the longitudinal axis of channel 2, whereby the exit aperture 7 of said nozzle 3 is oriented in the direction of aperture 4 and the patient. Nozzle 3 further projects radially outward from channel 2 a sufficient distance to form nipple 8. Flexible rubber tubing (not shown) is attached to nipple 8, thereby connecting device 1 to a remote reservoir (not shown) of pressurized gas. By regulating the mass flow rate of said gas into nozzle 3 through entrance aperture 6, variable levels of constant positive airway passage pressure can be maintained. An embodiment of device 1 using a constant inner diameter of 2 mm. for nozzle 3 has proven to be sufficient to permit the achievement of 5 to 20 cm. of $H_2O$ positive pressure in the airway passages of patients using the device.

In normal use inspired and expired air communicates to a patient through channel 2. Inasmuch as channel 2 presents an essentially unobstructed flow path to the aspired gas, the danger of back pressure buildup, created when the patient coughs, is eliminated. Still further, the absence of obstruction within the flow path permits the insertion of endotracheal suction apparatus through channel 2 while the device is being used. Finally, inasmuch as the expired gas exits the device through aperture 5, and does not flow back through nozzle 3 to the remote reservoir, the danger of infectious contamination of the tubing used to connect the device with the remote gas reservoir is significantly reduced.

DESCRIPTION OF AN ALTERNATE EMBODIMENT

Figure 2:
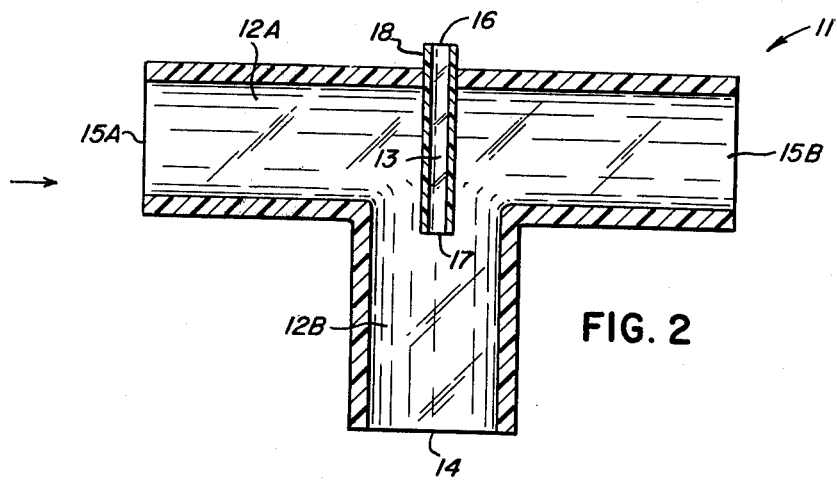
FIG. 2 is a plan cross-sectional view of an alternate embodiment of my invention.
Figure 3:
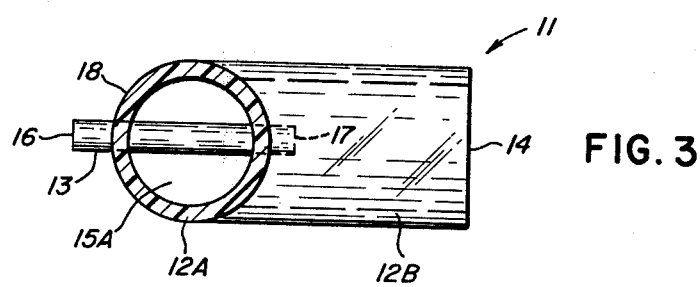
FIG. 3 is a side view of the embodiment shown in FIG. 2 in the direction of the arrow.

FIGS. 2 and 3 respectively represent cross-sectional plan and side views of an alternate embodiment of the present invention, particularly suitable for the use with a patient requiring the administration of controlled and conditioned gas.

This embodiment, generally denoted as 11, comprises a hollow, thin walled, cylindrical channel 12A, a second cylindrical channel 12B perpendicularly attached to channel 12A, and a narrow diameter nozzle 13.

Figure 4:
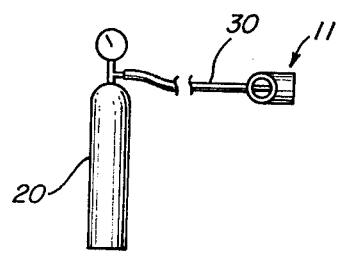
FIG. 4 is a somewhat diagrammatical side view of the embodiment shown in FIGS. 2 and 3 adapted to deliver positive pressure breathing gas to a patient.

Channel 12A further includes apertures 15A and 15B through which inspired gas enters and exits device 11. Gases flowing through the device are communicated to the patient through aperture 14 of channel 12B. Both channels 12A and 12B are of identical inner diameter, nominally 7-10 mm., and serve to provide a continuous unobstructed flow path. Radially interposed through channel 12A is a narrow diameter nozzle 13 oriented along the longitudinal axis of channel 12B and possessing an exit aperture 17 aligned in the direction of outlet aperture 14 and the patient. Said nozzle 13 further projects radially outward from the outer wall of channel 12A a sufficient distance to form nipple 18, thereby permitting the device to be attached to a remote reservoir 20 of pressurized gas by means of flexible tubing 30 (FIG. 4).

In all other respects the manner and use of the device 11 is identical to the disclosure contained in the preferred embodiment.

While I have illustrated and described several embodiments of the present invention, it is understood that various changes and modifications may be made in the detail thereof without departing from the scope of the invention as set forth in the appended claims. Such variant forms are therefore considered to be within both the essence and scope of my present invention.

What is claimed is:

1. An apparatus adapted for use on external airway passages of a patient having difficulty breathing to continuously infuse a steady state stream of pressurized gas into said airway passages whereby to create constant positive pressure therein, consisting essentially of:
   (a) a first conduit, of substantially constant inner diameter and defining a substantially unobstructed flow path therethrough, comprising first and second cylindrical members secured substantially perpendicular to each other whereby to form a "T" junction, said first cylindrical member having inlet apertures at each end thereof communicating with ambient air and said second cylindrical member having an outlet aperture at one end thereof adapted to receive connective members for communication with said airway passages, said first conduit further having an internal volume substantially less than the total volume of air expired by the patient;
   (b) a second conduit of substantially smaller diameter than said first conduit comprising a rigid nozzle disposed through the wall of said first conduit and terminating at a point intermediate the length thereof, said nozzle having an entrance aperture external and proximate to said wall and an exit aperture disposed within said first conduit substantially directed towards said outlet aperture; and
   (c) means for infusing a steady state stream of gas into said second conduit.

2. An apparatus adapted for use on external airway passages of a patient having difficulty in breathing to continuously infuse a steady state stream of pressurized gas into said airway passages whereby to create constant positive pressure therein, consisting essentially of:
   (a) a first conduit, defining a substantially unobstructed flow path therethrough, comprising first and second hollow members secured substantially perpendicular to each other whereby to form a "T" junction, said first hollow member having inlet apertures at each end thereof communicating with ambient air and said second hollow member having an outlet aperture at one end thereof adapted to receive connective members for communication with said airway passages, said first conduit further having an internal volume substantially less than the total volume of air expired by a patient;
   (b) a second hollow conduit of substantially smaller cross-sectional area than said first hollow conduit comprising a rigid nozzle disposed through the wall of said first conduit and terminating at a point intermediate the length thereof, said nozzle having an entrance aperture external and proximate to said wall and an exit aperture disposed within said first conduit directed substantially towards said outlet aperture; and
   (c) means for infusing a steady state stream of gas into said second conduit.

3. An apparatus as set forth in claim 1 or 2 wherein said infusing means comprises a reservoir of pressurized gas remote from said first and second hollow conduits and tubing means communicating between said reservoir and said entrance aperture.

4. A method for creating constant positive pressure within the airway passages of a patient, comprising the steps of:
   (a) connecting an apparatus as set forth in claim 1 or claim 2 to the airway passages of a patient; and
   (b) controllably infusing a steady state stream of gas through said second conduit and into said air way passages whereby to create positive pressure therein.

* * * * *